US007531677B2

(12) United States Patent
Choo et al.

(10) Patent No.: US 7,531,677 B2
(45) Date of Patent: May 12, 2009

(54) HIGH PURITY PALM MONOGLYCERIDES

(75) Inventors: Yuen May Choo, Petaling Jaya (MY); Sit Foon Cheng, Johor (MY); Ah Ngan Ma, Selangor (MY); Yusof Basiron, Petaling Jaya (MY)

(73) Assignee: Lembaga Minyak Sawit Malaysia, Kajang (MY)

( * ) Notice: Subject to any disclaimer, the term of this patent is extended or adjusted under 35 U.S.C. 154(b) by 0 days.

(21) Appl. No.: 11/232,461

(22) Filed: Sep. 21, 2005

(65) Prior Publication Data

US 2006/0128979 A1 Jun. 15, 2006

(30) Foreign Application Priority Data

Dec. 10, 2004 (MY) ............................. PI 2004 5102

(51) Int. Cl.
*C07C 51/43* (2006.01)

(52) U.S. Cl. ...................................................... 554/174

(58) Field of Classification Search .................. 554/168
See application file for complete search history.

(56) References Cited

U.S. PATENT DOCUMENTS

| | | | | |
|---|---|---|---|---|
| 2,251,692 | A * | 8/1941 | Richardson | 554/173 |
| 2,608,564 | A | 8/1952 | Young et al. | |
| 2,789,119 | A * | 4/1957 | Sully | 554/168 |
| 3,079,412 | A * | 2/1963 | Chang et al. | 554/168 |
| 6,127,561 | A * | 10/2000 | Jeromin et al. | 554/169 |

FOREIGN PATENT DOCUMENTS

GB 763474 2/1954

OTHER PUBLICATIONS

Choudhury, Journal of the American Oil Chemist, vol. 39, pp. 345-347, 1962.*
European Search Report Application No. EP 05 25 5947.

* cited by examiner

*Primary Examiner*—Deborah D Carr
(74) *Attorney, Agent, or Firm*—Ladas and Parry LLP

(57) ABSTRACT

The present invention relates to a process for producing high purity monoglycerides from edible oils/fats and fatty acids through glycerolysis, in particular but not exclusively to the production of monoglycerides from palm oil and palm oil products. This is achieved by providing a process for the production of monoglycerides of fatty acids or fats and oils, comprising the steps of reacting fatty acids or fats and oils with excess glycerol in the presence of an acidic or alkaline catalyst; substantially separating the crude reaction product from the other reaction components; removing unwanted reaction components from the crude reaction product by washing; drying the reaction product.

29 Claims, 4 Drawing Sheets

Scheme 2

*for quenching reaction

Scheme 3

- for stopping reaction

Scheme 4

HIGH PURITY PALM MONOGLYCERIDES

FIELD OF INVENTION

The present invention relates to a process for producing high purity monoglycerides from edible oils/fats and fatty acids through glycerolysis, in particular but not exclusively to the production of monoglycerides from palm oil and palm oil products.

BACKGROUND ART

Partial glycerides are commercially synthesized on a considerable scale every year for use as emulsifying agents in a wide range of foods. Monoglycerides in particular, which have superior emulsifying property than diglycerides, account for over 70% of the total world consumption of food emulsifiers. In general, the technical monoglycerides are not pure monoglycerides, but generally consists of a mixture of 40-48% monoglycerides, 30-40% diglycerides, 5-10% triglycerides, 0.2-9% fatty acids and 4-8% glycerol. Pure monoglycerides are available only after isolation by molecular distillation of the technical monoglycerides (Meffert, 1984). These pure monoglycerides are obviously more expensive as compared to the technical products. Their most important application is in food industry due to their excellent self-emulsifying and surface-active properties. Particular types of monoglycerides such as monolaurin, monocaprin and the like are in use as anti microbial agents or antiseptic agents, e.g. for foods and pharmaceutical industry.

Both monoglycerides and their derivatives, in addition to their excellent emulsifying properties, are also used in non-food applications such as emulsifiers, texturing agents, lubricants and plasticizers in pharmaceuticals, cosmetics and textiles etc. Depending on the chain length of the fatty acid monoglycerides, they are encountered in various formulations and usage in the non-food products and application.

Generally, there are two routes to the production of monoglycerides, namely the chemical and enzymatic synthesis. Glycerolysis of fats and oils or fatty acids are preferred since the partial esters of glycerol enjoy considerably more applications than those derived from glycol. On an industrial scale, monoglycerides are usually produced by glycerolysis of natural oils and fats with glycerol at temperatures greater than 220° C. in the presence of an inorganic catalyst, the reaction products are in an equilibrium mixture consisting of monoglycerides, diglycerides and triglycerides (Sonntag, 1982). However, in general, glycerides used as emulsifiers are required to contain at least about 90 mole % of monoglycerides. Hence, in the conventional production of such glycerides, it has been necessary to subject a glyceride mixture to molecular distillation or the like to enhance the content of monoglycerides. The yield of the conversion of triglycerides to monoglycerides is about 58%. Some studies using various solvents to improve the homogeneity of the reactants, i.e glycerol and fats have also been carried out. A total yield of 83% monoglycerides has been obtained using pyridine as a solvent for the glycerolysis of sunflower seed oil. Solvents offer the prospect of high yield of monoglycerides at relatively low temperature. But due to various drawbacks, glycerolysis involving solvent has not been studied extensively.

U.S. Pat. No. 6,127,561 discloses a process for the production of monoglycerides based on the glycerolysis of methyl ester derived from animal and vegetable fats and oils. The reaction was carried out at between 130 to 160° C. at a vacuum of 200 to 400 mbar, using an alkaline catalyst, stopping the reaction by fast cooling of the reaction mixture and the destruction of the catalyst when the quantity of glycerides has reached a concentration of mono and diglyceride of 40-60% and the ratio of concentration of mono and diglyceride lies between 3 to 10.

G.B. Patent 950,667 also discloses a process for the preparation of monoglycerides via glycerolysis of a mixture of glycerine and fatty acids or their esters or other mono- or polyvalent alcohols provided that the other alcohols are more volatile than glycerine at a temperature of at least 260° C. The reaction products comprising glycerine and a glyceride having high monoglycerides content are separated into two layers by cooling, one layer comprising glycerine which is removed. Residual glycerine is removed from the other layer by distillation and followed by water-washing to obtain the monoglycerides.

The production of monoglycerides via chemical synthesis can be further improved by engaging a suitable solvent to increase the solubility of glycerol in the oil and subsequently enhance the glycerolysis process.

For example, phenol was proposed by T. P Hilditch (1935) and J. G Riggs (1774). The reaction need to be carried out at a high temperature and in addition to that, it has been found out that phenol undergoes some condensation with stearic acid and glycerol, thus, giving rise to impurities which are not readily separated.

K. F Martill (1952) and R. J. Sims (1952) have proposed the use of tertiary aromatic amine such as pyridine, the picolines or isoquinoline as solvent for the reaction. However, these solvents caused difficulties due to odour and toxicity.

U.S. Pat. No. 2,789,119 discloses a process for the preparation of monoglycerides from naturally occurring fatty oil, fats or artificially prepared esters of higher fatty acids (which are substantially insoluble in water) in the presence of tertiary butyl alcohol and an alkaline catalyst. According to the patent disclosure, tertiary butyl alcohol is an excellent reaction medium and that is not esterified by fatty acid under the reaction condition. It is non-toxic, relatively odourless and has a low boiling point, making it readily removed from the reaction mixture. It is dehydrated under acid conditions and is therefore used in inter-esterification process between neutral fatty glycerides and glycerol with an alkaline catalyst.

In recent years, synthesis of monoglycerides using lipase enzymes has been actively investigated. Studies using a wide variety of different enzymes and substrates as well as conditions to improve the yield of partial glycerides have been carried out. U.S. Pat. No. 5,270,188 discloses a process of preparation of glycerides having a high content of monoglycerides with a lipase from Penicilium cyclopium ATCC 34613. Monoglycerides are produced by mixing glycerol and fatty acids with the lipase under agitation at a temperature of 20-55° C. for 1-50 hours.

Stevenson et al. (1993) have also investigated the glycerolysis of tallow with immobilized lipase. In 'Glycerolysis of Tallow with Immobilised Lipase' published in Biotechnology Lett. 15, 1043-1048, they have revealed the glycerolysis of melted tallow by using Lipozyme (immobilized *Mucor meihei* lipase) to synthesize monoglycerides. When reaction was carried out at 50° C., a maximum 35% yield of monoglyceride was obtained. Cooling before 42° C. resulted in monoglycerides crystallisation which improved the yield up to 50% but further yield was prevented by solidification of the reaction mixture. Although the present invention is embodied in several different aspects it will be clear from this broad background review that each aspect is so linked as to form part of the same inventive concept.

STATEMENTS OF THE INVENTION

According to a first aspect of the present invention there is provided a process for the production of monoglycerides of fatty acids or fats and oils, comprising the steps of:

reacting fatty acids or fats and oils with excess glycerol in the presence of an acidic or alkaline catalyst; substantially separating the crude reaction product from the other reaction components through means other than distillation;

removing unwanted reaction components from the crude reaction product by washing;

drying the reaction product.

Preferably the process uses a reaction solvent

More preferably the reaction solvent used is tert-butanol.

Preferably, drying of the reaction product is via vacuum drying.

Preferably, the separation step involves the use of an organic solvent.

More preferably, the solvent is a non polar solvent.

Even more preferably, the solvent is a linear alkane.

Yet more preferably, the solvent is hexane.

Yet more preferably still, the solvent used during the separation step is above room temperature.

Preferably, the separation step involves crystalisation of the reaction product.

Preferably, the drying of the reaction product involves vacuum distillation of unwanted impurities.

Preferably, the fatty acids are those derived from vegetable fats and oils, ranging from carbon chain length $C_6$-$C_{20}$.

Preferably, the fats and oil are those derived from vegetable and animal origin and may be selected from the group comprising palm derived, namely palm oil, palm oil products, palm kernel oil, palm kernel products, soy bean oil, olive oil, coconut oil, rapeseed oil, corn oil and sunflower oil.

Preferably, the molar ratio of glycerol to fatty acids is in the range of 1 to 4.

Preferably, the weight ratio of oil to glycerol is in the range of 1 to 4.

Preferably, removing unwanted reaction components from the crude reaction product by washing involves washing with distilled water.

Preferably, the reaction solvent is recovered and recycled for re-use.

Preferably, the volume:weight ratio of reaction solvent to oil is from 1 to 2.

Preferably, the catalyst used is an organic alkali or acid.

Preferably, the acidic catalyst used can be selected from the group comprising sulphuric acid, sulfonic acid and acidic ion-exchange resins.

Preferably, the alkaline catalyst used can be selected from the group comprising an alkali metal sodium methoxide, potassium hydroxide and sodium hydroxide.

Preferably, the alkaline catalyst used can be selected from the group comprising an alkali metal methoxide and hydroxide.

Preferably, the alkali metal is potassium or sodium.

Preferably, the catalyst concentration is in the range of zero to 3% weight of the fatty acids or fats and oils.

Preferably, the said process is to be carried out at a temperature in the range of about 80 to about 170° C.

Preferably, the temperature range is in the range of about 90 to about 160° C.

Preferably, the process produces at least 80% monoglycerides in the reaction mixture before purification.

Preferably, the monoglycerides obtained from the process contained monoglycerides of at least 97% purity after purification.

Preferably, the volume:weight ratio of the reaction solvent to the fatty acids is in the range of 1 to 4.

Preferably a process as indicated in specific example 1 described herein is intended to be protected.

Preferably a process as indicated in specific example 2 described herein is intended to be protected.

Preferably a process as indicated in specific example 3 described herein is intended to be protected.

Preferably a process as indicated in specific example 4 described herein is intended to be protected.

Preferably a process as indicated in specific example 5 described herein is intended to be protected.

Preferably a process as indicated in specific example 6 described herein is intended to be protected.

Preferably a process as indicated in specific example 7 described herein is intended to be protected.

Preferably a process as indicated in specific example 8 described herein is intended to be protected.

Preferably a process as indicated in specific example 9 described herein is intended to be protected.

According to a second aspect of the present invention, there is provided a substantially pure monoglyceride product formed according to the process as claimed in any of the process claims.

According to a third aspect of the present invention there is provided a use of the monoglyceride synthesized according to the process for the manufacture of a medicament for therapeutic application as an anti-bacterial agent.

According to a fourth aspect of the present invention, there is provided a use of the monoglyceride synthesized according to the process for the manufacture of a medicament for therapeutic application as an anti methicillin-resistant *Staphylococcus aureus* (MRSA) agent.

According to a fifth aspect of the present invention there is provided a use of the monoglyceride synthesized according to the process for the manufacture of an emulsifier, plasticiser or texturing agent.

BRIEF DESCRIPTION OF THE DRAWINGS

Preferred embodiments of the present invention will now be more particularly described by way of example only, with reference to the accompanying sheets of drawings in which.

DETAILED DESCRIPTION OF PRESENT INVENTION

Figure 1:
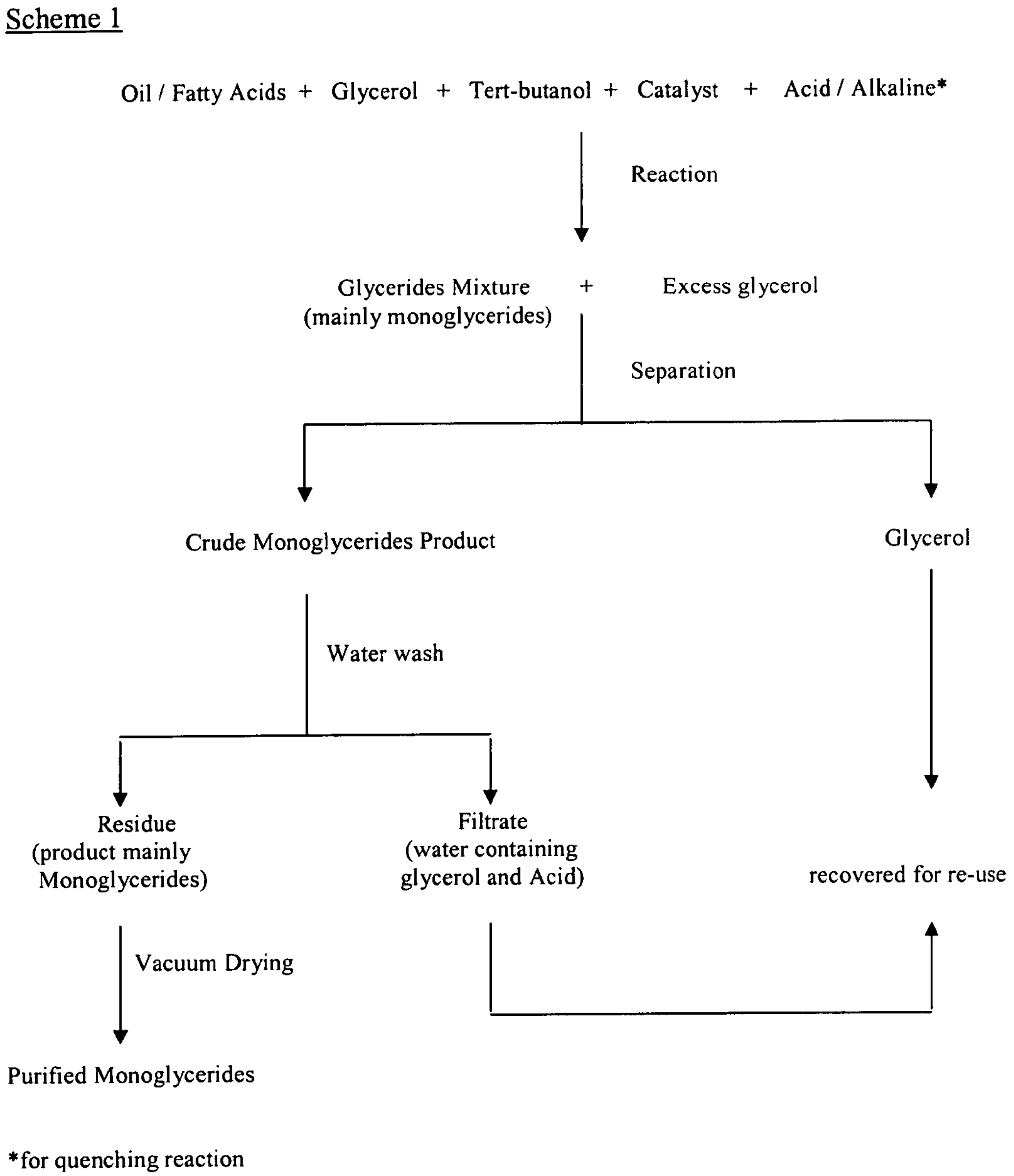
FIG. 1 is one schematic representing one embodiment of a process covered by the present invention.

The present invention provides a process for producing high purity of monoglycerides from edible oils and fats through glycerolysis. More particularly but not exclusively, the present invention relates application to the production of monoglycerides from palm oil and palm oil products and palm-based fatty acids. Most preferably, the present invention relates to a process for preparing high purity of monoglycerides by reacting a fatty acid or fats and oils with glycerol in the presence of an inorganic or organic catalyst with or without the presence of solvent. These monoglycerides have wide technical uses, they are particularly useful as emulsifiers and anti microbial agents, as well as texturing agents, lubricants and plasticizers in pharmaceuticals, cosmetics and textiles etc. Depending on the chain length of the fatty acid monoglycerides, they are encountered in various formulations and usage in the non-food products and application.

The present invention leads to a convenient and efficient process for the production of monoglycerides in high yields and in much shorter time and lower temperature (90-160° C.) as compared to current technology of much longer reaction time and temperature of 180-220° C. Most importantly, the high purity (>90%) monoglycerides was produced without going through the molecular distillation step.

The advantages of the process according to the present invention mainly lies in the fact that the reaction temperature for carrying out the glycerolysis reactions can be distinctly reduced compared with the prior art without the conversion yield and purity suffering thereby. Intensive thorough mixing of the reaction mixture aids in the achievement of the results of this invention. The addition of solvent further enhances the homogeneity of the reaction mixtures.

At the same time, it is important to remove the water formed immediately during the process. This is done by using the Dean and Stark trap or optionally at reduced pressure or supported by an inert gas stream purge into the reaction flask. The use of solvent in the process has additional advantage in this aspect of the invention and must be mentioned as the presence of solvent will assists the removal of water.

According to the present invention, the ratio of monoglycerides and diglycerides in the glycerides synthesized can be varied widely by selecting reaction conditions appropriately, namely the ratio of the starting materials, temperature, catalyst, concentration of catalyst and reaction time. In the case when solvent is employed in the process, the reaction mixture upon completion according to the present invention can be separated by leaving it on standing, whereby the upper layer contains the desired glycerides mixture and the lower layer contains mainly excess glycerol and unreacted fatty acids. Whereas in the case where solvent is employed as a reaction medium, there will be no separation as it is in the previous case where no solvent is employed. In order to synthesize substantially only monoglycerides, it is preferable that the glycerides mixture synthesized is subjected to purification steps.

Therefore, the crude monoglyceride product and unreacted starting materials were subjected to the following steps:

(a) The product was solidified when cooled on standing. The solid product was then washed with distilled water to remove excess glycerol as well as the citric/acetic acid or sodium carbonate (as neutralising agent to the basic/acid catalyst used). This washing sequence was repeated for three times consecutively. The product containing mainly monoglycerides were further vacuum dried. This particular step produces monoglycerides without any impurities. Glycerol found mainly in the filtrate can be recovered for re-use by removing the water present. The procedure is depicted in Scheme 1.

(b) The solidified product was washed with hexane to remove less polar impurities, followed by distilled water to remove glycerol and inorganic acidic acid. This washing sequence was repeated for three times consecutively. The final product was white crystalline containing mainly monoglycerides. The product was subjected to vacuum drying. The procedure is depicted in Scheme 2.

(c) The solidified product was subjected to water wash to remove excess glycerol and acid used in the process. This washing sequence was repeated for three times consecutively. The washed product was then subjected to vacuum distillation to remove less polar impurities. The procedure is depicted in Scheme 3.

(d) The solidified product was dissolved in hexane at 60° C. Crystallisation was then carried out using temperature gradient from 60° C. to 20° C. Crystals appeared at about 37° C. and were filtered, water washed and dried. The procedure is depicted in Scheme 4.

Figure 2:
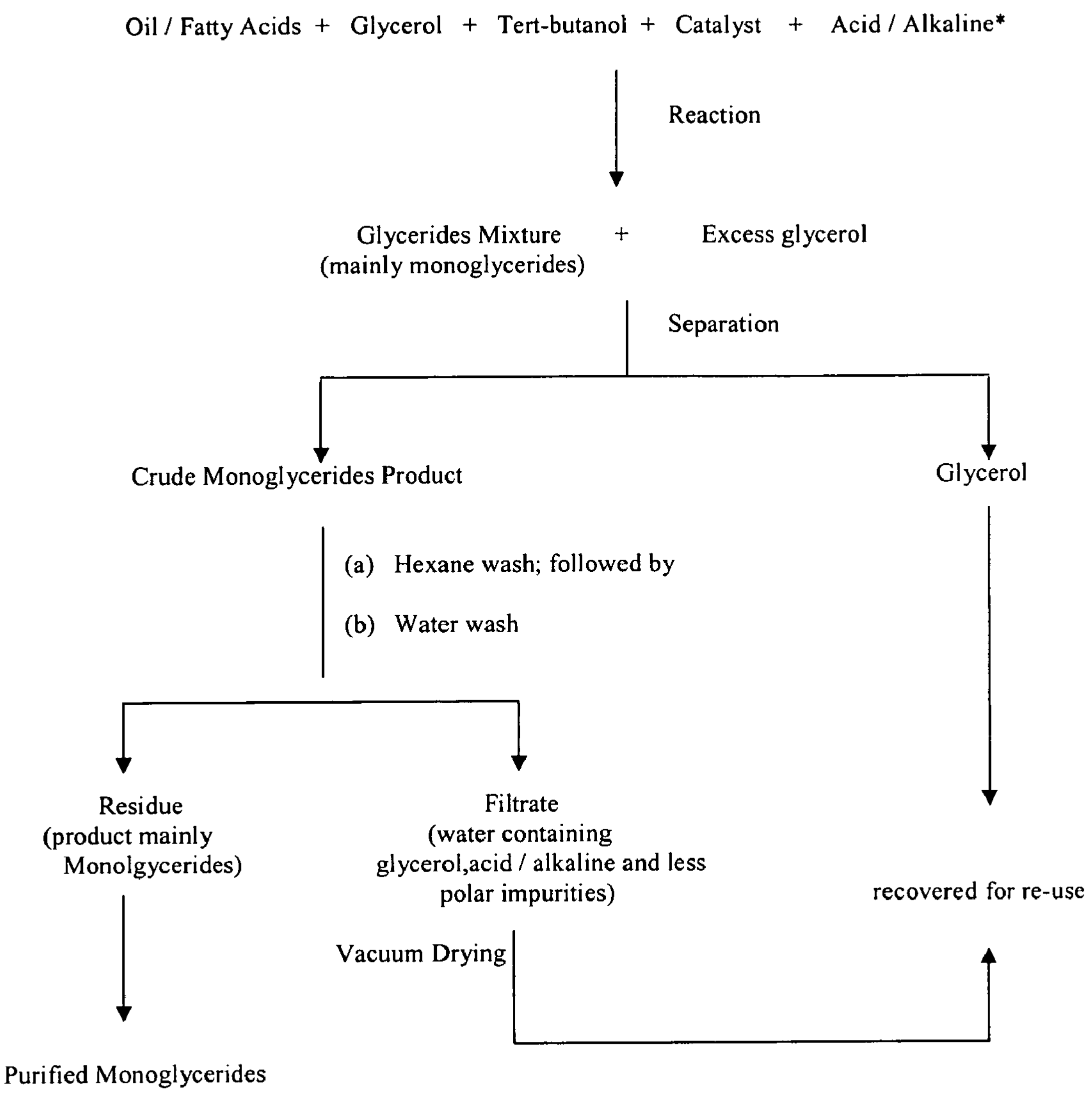
FIG. 2 is another schematic representing another embodiment of a process covered by the present invention.
Figure 3:
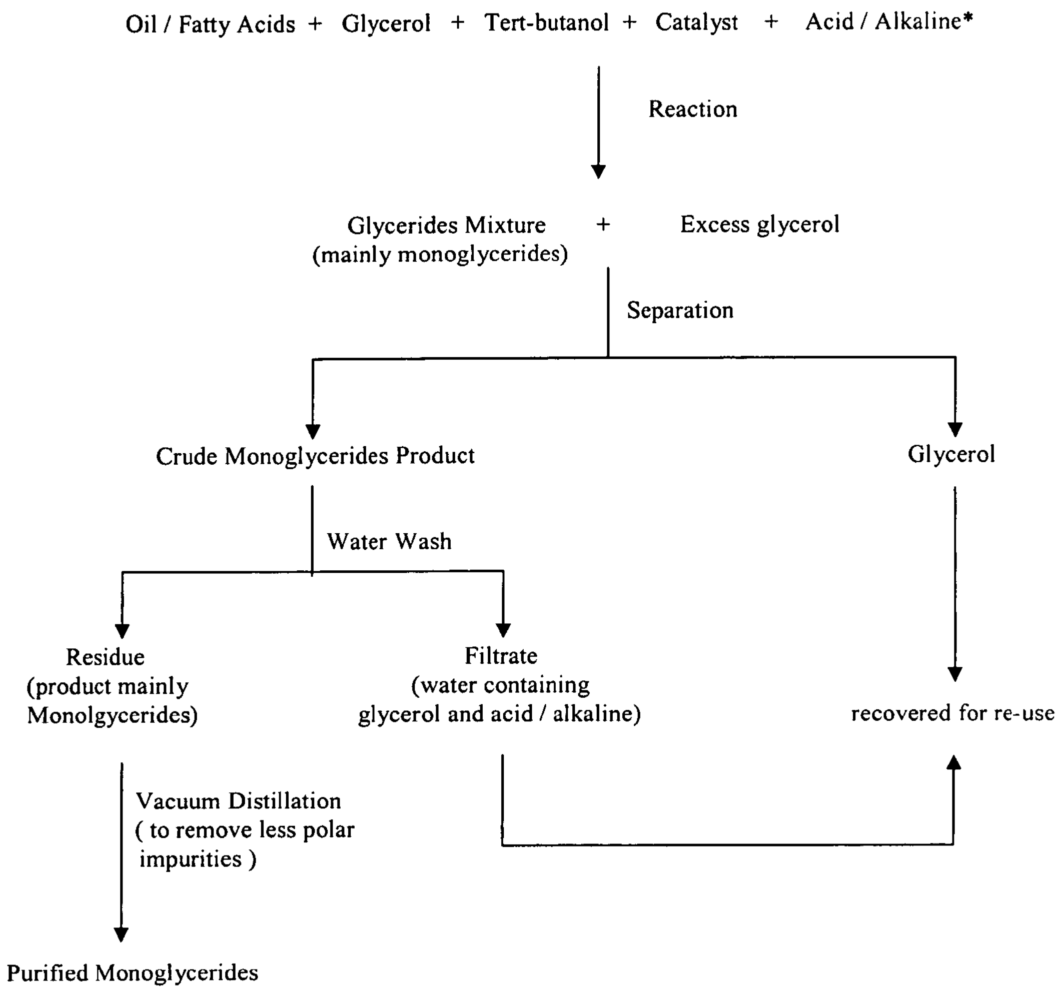
FIG. 3 is yet another schematic representing yet another embodiment of a process covered by the present invention
Figure 4:
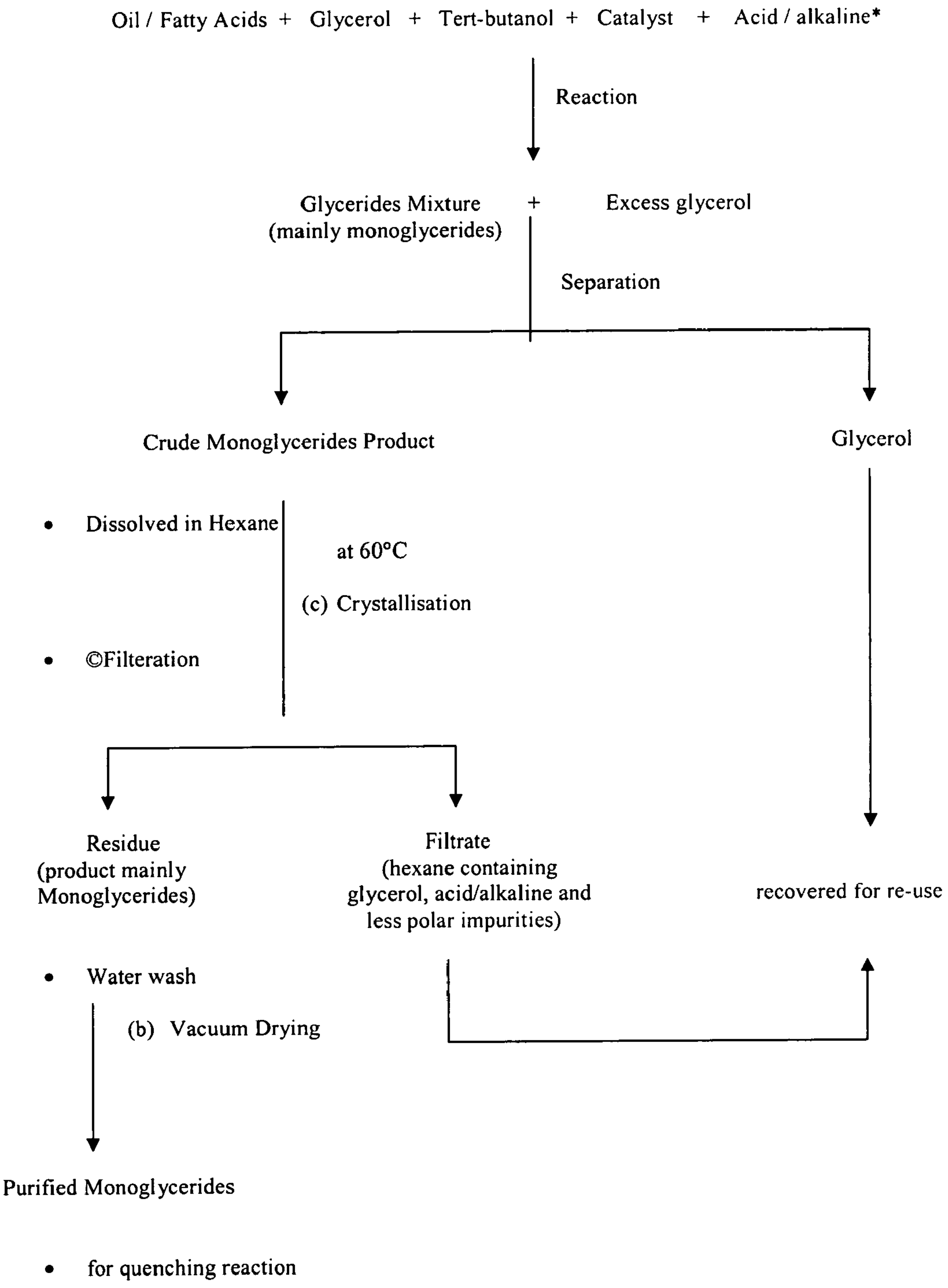
FIG. 4 is a final schematic representing a last embodiment of a process covered by the present invention

According to scheme or FIG. 2, some of the purification steps provided were by washing the glyceride mixtures with (1) water and/or (2) hexanes. This particular step is able to improve the purity of monoglycerides to >99%, substantially free of diglycerides and triglycerides.

The reaction progress in the present invention was monitored through composition analysis using gas chromatography and thin layer chromatography. The reaction aliquots were withdrawn during the reaction mixture As soon as the samples were withdrawn the catalytic action of acid catalyst was terminated by neutralising it with diluted sodium carbonate and those of alkaline catalyst was terminated by using acetic or citric acid. The organic layer was kept with anhydrous sodium sulphate overnight to absorb water left in the samples.

The present invention is further illustrated but not limited by the following examples.

EXAMPLE 1

A 0.25 g of sodium hydroxide was dissolved in 25 g glycerol (anhydrous or predried under vacuum). The mixture was then dried under vacuum at above 100° C. with vigorous stirring. This was then added to a mixture containing 25 g of hydrogenated palm stearin and 50 ml of tert-butanol (dried over molecular sieves) and the reaction was conducted at 90° C. for 1 hour. Aliquot of samples from the reaction mixture were withdrawn at different time intervals i.e. 1, 3, 5, 7, 10, 20, 30 and 60 minutes for compositon analysis of respective glycerides formed. The conversion of oil to monoglycerides was monitored by gas chromatography. The reaction was stopped by quenching with citric acid or acetic acid.

The excess tert-butanol was recovered from the final product. The upper layer contained mainly glycerides mixtures while the lower layer contained mainly glycerol. The glycerol can be recovered and use in the subsequent processes.

The solidified product upon cooling on standing was washed with distilled water at ratio 1:3 for three times to remove excess glycerol and citric or acetic acid. The product which white in colour was subjected to vacuum to further removed moisture.

The proportion of monoglycerides reached 80% or more above 7 minutes of reaction.

The results are tabulated in Table 1.

TABLE 1

Glycerolysis of Hydrogenated Palm Stearin with NaOH as Catalyst

| Reaction Time | Composition of Reaction Mixture (%) | | | |
|---|---|---|---|---|
| (min) | MG | DG | TG | FFA |
| 0 | 0 | 5.1 | 92.4 | 2.5 |
| 3 | 58.6 | 14.6 | 22.6 | 4.1 |
| 5 | 71.2 | 15.6 | 9.1 | 4.1 |

TABLE 1-continued

Glycerolysis of Hydrogenated Palm Stearin with NaOH as Catalyst

| Reaction Time | Composition of Reaction Mixture (%) | | | |
|---|---|---|---|---|
| (min) | MG | DG | TG | FFA |
| 7 | 91.4 | 4.2 | 0 | 4.4 |
| 10 | 85.2 | 10.2 | 0 | 4.6 |
| 20 | 85.7 | 12.0 | 0 | 2.3 |
| 30 | 85.0 | 11.8 | 0 | 3.2 |
| 60 | 85.4 | 11.9 | 0 | 2.7 |

Reaction Temperature: 90° C.
Catalyst: Sodium Hydroxide
Catalyst Concentration (weight percent based on the weight of oil): 1%
Oil:Glycerol (w/w) ratio = 1:1
Oil:Solvent (t-butanol) (w/v) ratio = 1:2

EXAMPLE 2

The procedures of Example 1 were repeated except sodium methoxide was used as the catalyst. Under those reaction conditions, the content of monoglycerides synthesized was above 80% after 30 minutes of reaction. The results are tabulated in Table 2.

TABLE 2

Glycerolysis of Hydrogenated Palm Stearin with NaOMe as Catalyst

| Reaction Time | Composition of Reaction Mixture (%) | | | |
|---|---|---|---|---|
| (min) | MG | DG | TG | FFA |
| 15 | 41.8 | 10.1 | 45.5 | 2.6 |
| 30 | 85.9 | 10.9 | 0 | 3.3 |
| 60 | 85.9 | 11.2 | 0 | 2.9 |
| After Quench | 87.2 | 8.3 | 0 | 4.5 |
| After Washing | 86.6 | 9.6 | 1.0 | 2.7 |

Reaction Temperature: 90° C.
Catalyst: Sodium Methoxide (NaOMe)
Catalyst Concentration (weight percent based on the weight of oil): 1%
Oil:Glycerol (w/w) ratio = 1:1
Oil:Solvent (t-butanol) (w/v) ratio = 1:2

EXAMPLE 3

The procedures of Example 1 were repeated except potassium hydroxide was used as the catalyst. Under those reaction conditions, the content of monoglycerides synthesized was above 80% after 7 minutes of reaction and based on the on the results, the duration of the reaction can be chosen depending on the desired glycerides composition. The results are tabulated in Table 3.

TABLE 3

Glycerolysis of Hydrogenated Palm Stearin with KOH as Catalyst

| Reaction Time | Composition of Reaction Mixture (%) | | | |
|---|---|---|---|---|
| (min) | MG | DG | TG | FFA |
| 3 | 65.4 | 16.6 | 13.8 | 4.2 |
| 5 | 64.7 | 21.0 | 11.4 | 2.8 |
| 7 | 81.2 | 13.6 | 1.6 | 3.6 |
| 10 | 76.1 | 17.1 | 3.7 | 3.1 |
| 15 | 81.2 | 11.9 | 2.6 | 4.3 |
| 20 | 79.4 | 15.1 | 0.6 | 4.9 |

TABLE 3-continued

Glycerolysis of Hydrogenated Palm Stearin with KOH as Catalyst

| Reaction Time | Composition of Reaction Mixture (%) | | | |
|---|---|---|---|---|
| (min) | MG | DG | TG | FFA |
| 30 | 82.0 | 12.1 | 0.7 | 5.0 |
| 40 | 80.0 | 14.9 | 0.7 | 5.1 |
| 50 | 79.4 | 14.7 | 0.7 | 5.1 |
| 60 | 77.8 | 16.6 | 0.7 | 5.0 |
| 120 | 78.0 | 16.3 | 0.4 | 5.3 |
| After Quench | 81.0 | 11.4 | 0.6 | 6.9 |

Reaction Temperature: 90° C.
Catalyst: Potassium Hydroxide (KOH)
Catalyst Concentration (weight percent based on the weight of oil): 1%
Oil:Glycerol (w/w) ratio = 1:1
Oil:Solvent (t-butanol) (w/v) ratio = 1:2

EXAMPLE 4

The procedure of Example 1 were repeated except sodium methoxide was used as the catalyst (0.6%) and RBD Palm Olein was used as the starting material. Under those reaction conditions and after 90 minutes of reaction, the reaction mixture contains 3.9% fatty acids, 1.0% esters, 68.5% monoglycerides, 15.1% diglycerides and 11.4% triglycerides.

EXAMPLE 5

A 100 g of lauric acid and 184 g of anhydrous glycerol (molar ratio of oil:glycerol=1:4) were mixed with 400 ml of t-butanol (oil: solvent (w/v) ratio=1:4). The mixture was heated on a heating plate with contact thermometer set at the required temperature. A magnetic stirrer was used to agitate the mixture. A 0.5 g of p-toluenesulfonic acid (p-TSA) was added to the reaction mixture and the mixture was refluxed for 5 hours. Samples of the reaction mixture were withdrawn at 10, 20, 30 minutes and thereafter at 0.5 hours interval for composition analysis. The results of the optimal conditions for the preparation of the monoglycerides and diglycerides are shown in Table 5.

TABLE 5

Glycerolysis of Lauric Acid with p-TSA as Catalyst and using t-butanol as Solvent

| Reaction Time | Composition of Reaction Mixture (%) | | | |
|---|---|---|---|---|
| (min) | MG | DG | TG | FFA |
| 10 | 15 | — | — | 85 |
| 20 | 22 | — | — | 78 |
| 30 | 30.3 | — | — | 69.7 |
| 60 | 49.6 | 0.3 | — | 50.1 |
| 90 | 57.1 | 0.5 | — | 42.4 |
| 150 | 63.4 | 0.8 | — | 35.8 |
| 180 | 68.8 | 1.1 | — | 30.2 |
| 240 | 75.5 | 1.6 | — | 22.9 |
| 300 | 78.9 | 1.9 | — | 19.2 |

Reaction temperature: 160° C.
Catalyst: p-toluenesulfonic acid (p-TSA)
Catalyst Concentration (weight percent based on the weight of fatty acid): 0.5%
Fatty Acid:Glycerol molar ratio = 1:4
Fatty Acid:Solvent (t-butanol) (w/v) ratio = 1:4

Two (2) parts of hexane was added into one (1) part of final product. The mixture was stirred for 10 minutes. Then the resultant was filtered and washed with water. The filtrate was stirred for another 10 minutes and then filtered. The white crystalline was dried under vacuum.

The white crystalline was analysed by gas chromatography and the composition was 99.7% of monolaurin and 0.3% of glycerol.

EXAMPLE 6

Procedures in Example 5 were repeated except no solvent was used. The reaction was carried out under partial vacuum of 450 mmHg at 120° C. for 45 minutes. The purification steps were similar to those in Example 5.

The white crystalline was analysed with gas chromatography and contained 93% monolaurin and 7% glycerol.

EXAMPLE 7

Procedures in Example 5 were repeated except catalyst, concentrated sulphuric acid ($H_2SO_4$) was used and without any solvent. The results are shown in Table 6.

TABLE 6

Glycerolysis of Lauric Acid with Concentrated $H_2SO_4$ as Catalyst (without solvent)

| Reaction Time | Composition of Reaction Mixture (%) | | | |
|---|---|---|---|---|
| (min) | MG | DG | TG | FFA |
| 1 | 12.3 | 0.3 | — | 87.4 |
| 3 | 21.3 | 0.6 | — | 78.1 |
| 6 | 27.1 | 0.8 | — | 72.1 |
| 9 | 33.7 | 1.0 | 0.005 | 65.2 |
| 12 | 40.6 | 1.1 | 0.01 | 58.3 |
| 15 | 43.6 | 1.2 | 0.01 | 55.2 |

TABLE 6-continued

Glycerolysis of Lauric Acid with Concentrated $H_2SO_4$ as Catalyst (without solvent)

| Reaction Time | Composition of Reaction Mixture (%) | | | |
|---|---|---|---|---|
| (min) | MG | DG | TG | FFA |
| 17 | 60.9 | 1.9 | 0.01 | 37.2 |
| 19 | 78 | 5.3 | 0.07 | 16.6 |

Reaction Temperature: 120° C.
Catalyst: Concentrated Sulphuric Acid ($H_2SO_4$)
Catalyst Concentration (weight percent based on the weight of fatty acid): 0.005%
Fatty Acid:Glycerol molar ratio = 1:4
Solvent: Nil

EXAMPLE 8

A 50 g lauric acid was reacted with 101 g of glycerol at 120° C. and under partial vacuum of 450 mmHg for 2.5 hours. No solvent and catalyst were employed. The purification of the final product was similar to those in Example 5. The white crystalline was analysed by gas chromatography and consists of 64.5% monolaurin, 27.0% dilaurin, 2.8% trilaurin and 5.6% glycerol.

EXAMPLE 9

Monolaurin samples (MC, MW and MX) synthesized using the present invention were subjected to bio-assay evaluation. Disc diffusion assay was adopted as preliminary evaluation of the compounds as anti methicillin-resistant *Staphylococcus aureus* (MRSA) agent. Four types of antibiotics were used as comparison: Vancomycin (Va), Rifampicin (RD), Chloamphenicol (C) and Gentamicin (CN). It was found that the highest percentages for the 3 compounds against the 8 isolates were recorded when Vancomycin was used as comparison. This may suggest that the mode of action was inhibitory of cell wall synthesis. The detailed results are presented in Table 7.

TABLE 7

Diameter of Inhibitory Zone (mm) of Selected Sample Against Methicillin-resistant *Staphylococcus aureus* (MRSA) Agent

| | CT184 | | | | D51 | | | | HIS87 | | | |
|---|---|---|---|---|---|---|---|---|---|---|---|---|
| Sample | Va | Rd | C | CN | Va | Rd | C | CN | Va | Rd | C | CN |
| MC | 2.79 | 0.42 | 0.82 | 0.35 | 2.95 | 0.11 | 0.87 | 0.86 | 2.79 | 0.11 | 0.84 | 0.96 |
| MW | 2.79 | 0.42 | 0.82 | 0.35 | 3.00 | 0.11 | 0.88 | 0.88 | 2.84 | 0.12 | 0.85 | 0.98 |
| MX | 2.95 | 0.44 | 0.87 | 0.37 | 3.04 | 0.11 | 0.90 | 0.89 | 2.92 | 0.12 | 0.87 | 1.01 |

| | SA | | | | SP521 | | | | ST122 | | | |
|---|---|---|---|---|---|---|---|---|---|---|---|---|
| Sample | Va | Rd | C | CN | Va | Rd | C | CN | Va | Rd | C | CN |
| MC | 2.92 | 0.40 | 2.00 | 0.40 | 7.64 | 1.13 | 2.68 | 1.13 | 8.26 | 1.17 | 5.50 | 1.17 |
| MW | 5.42 | 0.74 | 3.72 | 0.74 | 6.12 | 0.90 | 2.14 | 0.90 | 6.38 | 0.90 | 4.25 | 0.90 |
| MX | 3.00 | 0.41 | 2.06 | 0.41 | 3.08 | 0.45 | 1.08 | 0.45 | 3.00 | 0.42 | 2.00 | 0.42 |

| | N34 | | | | U949 | | | |
|---|---|---|---|---|---|---|---|---|
| Sample | Va | Rd | C | CN | Va | Rd | C | CN |
| MC | 2.99 | 0.44 | 0.89 | 0.44 | 7.77 | 1.02 | 4.73 | 1.02 |
| MW | 3.12 | 0.46 | 0.93 | 0.46 | 3.04 | 0.40 | 1.85 | 0.40 |
| MX | 3.04 | 0.45 | 0.90 | 0.45 | 2.86 | 0.38 | 1.74 | 0.38 |

* MC (99.7% monolaurin, 0.3% glycerol); MW (93% monolaurin, 7% glycerol); MX (64.5% monolaurin, 27.0% dilaurin, 2.8% trilaurin and 5.6% glycerol)

The invention claimed is:

1. A process for the production of monoglycerides of fatty acids or fats and oils, comprising the steps of:

(a) reacting starting materials comprising fatty acids or fats and oils, a reaction solvent and excess glycerol in the presence of an acidic or alkaline catalyst, with thorough mixing of the starting materials and with immediate removal of water formed during the reacting, to form a resultant product comprising a crude reaction product and other reaction components;

(b) substantially separating the crude reaction product from the other reaction components through means exclusive of distillation including by washing the crude reaction product with an organic solvent to remove impurities that are less polar than glycerol, said washing comprising adding the organic solvent to the crude reaction product after formation thereof;

(c) further removing unwanted reaction components from the crude reaction product by washing, with distilled water to form a final reaction product that consists essentially of the monoglycerides; and (d) drying the final reaction product, wherein said reacting in step (a) is carried out at a temperature, a ratio of the starting materials, a concentration of the acidic or alkaline catalyst and a reaction time such that, upon subjecting the crude reaction product to a purification in steps (b), (c), and (d), the final reaction product comprises the monoglycerides at a purity of at least 97%, said washing with organic solvent in step (b) and said washing with distilled water in step (c) being carried out with sufficient amounts of organic solvent and water respectively to obtain said monoglycerides of at least 97% purity.

2. A process as claimed in claim 1, wherein the reaction solvent is tert-butanol.

3. A process as claimed in claim 1, wherein drying of the final reaction product is via vacuum drying.

4. A process as claimed in claim 1, wherein the organic solvent is a non polar solvent.

5. A process as claimed in claim 1, wherein the organic solvent is a linear alkane.

6. A process as claimed in claim 1, wherein the organic solvent is hexane.

7. A process as claimed in claim 1, wherein the organic solvent is above room temperature.

8. A process as claimed in claim 1, wherein step (b) involves crystalisation of the crude reaction product.

9. A process as claimed in claim 1, wherein the drying of the final reaction product in step (d) involves vacuum distillation of unwanted impurities.

10. A process as claimed in claim 1, wherein the fatty acids comprise a carbon chain length of $C_6$-$C_{20}$.

11. A process as claimed in claim 1, wherein the fats and oil are those derived from vegetable and animal origin and are selected from the group consisting of palm derived, namely palm oil, palm oil products, palm kernel oil, palm kernel products, soy bean oil, olive oil, coconut oil, rapeseed oil, corn oil and sunflower oil.

12. A process as claimed in claim 1, wherein a molar ratio of glycerol to fatty acids is in the range of 1 to 4.

13. A process as claimed in claim 1, wherein a weight ratio of oil to glycerol is in the range of 1 to 4.

14. A process as claimed in claim 1, wherein the reaction solvent is recovered and recycled for re-use.

15. A process as claimed in claim 1, wherein a ratio of volume of the reaction solvent to weight of the oil is from 1 to 2.

16. A process as claimed in claim 1, wherein the acidic or alkaline catalyst used is organic.

17. A process as claimed in claim 1, wherein the acidic catalyst is selected from the group consisting of sulphuric acid, sulfonic acid and acidic ion-exchange resins.

18. A process as claimed in claim 1, wherein the alkaline catalyst is selected from the group consisting of an alkali metal methoxide, potassium hydroxide and sodium hydroxide.

19. A process as claimed in claim 1, wherein the alkaline catalyst is selected from the group consisting of an alkali metal methoxide and hydroxide.

20. A process as claimed in claim 19, wherein the alkali metal is potassium or sodium.

21. A process as claimed in claim 1, wherein the concentration of the acidic or alkaline catalyst is in the range of zero to 3% weight of the fatty acids or fats and oils.

22. A process as claimed in claim 1, wherein said process is carried out at a temperature in the range of about 80 to about 170° C.

23. A process as claimed in claim 22, wherein the temperature range is in the range of about 90 to about 160° C.

24. A process as claimed in claim 1, wherein the crude reaction product comprises at least 80% monoglycerides before the purification.

25. A process as claimed in claim 1, wherein the ratio of volume of the reaction solvent to weight of the fatty acids is in the range of 1 to 4.

26. The process of claim 1 further comprising incorporating the final reaction product into a medicament for therapeutic application as an anti-bacterial agent.

27. The process of claim 2 further comprising incorporating the final reaction product into a medicament.

28. The process of claim 1 further comprising incorporating the final reaction product into an emulsifier, plasticiser or texturing agent.

29. A process as claimed in claim 1, wherein the separation step (b) comprises dissolving the crude reaction product in the organic solvent.

* * * * *